United States Patent
Cabrera et al.

(10) Patent No.: US 10,117,675 B2
(45) Date of Patent: Nov. 6, 2018

(54) TROCAR TIP PROTECTOR

(71) Applicant: Covidien LP, Mansfield, MA (US)

(72) Inventors: Ramiro Cabrera, Cheshire, CT (US); Stephen Paul, East Hartford, CT (US); David Valentine, East Hampton, CT (US)

(73) Assignee: Covidien LP, Mansfield, MA (US)

( * ) Notice: Subject to any disclaimer, the term of this patent is extended or adjusted under 35 U.S.C. 154(b) by 514 days.

(21) Appl. No.: 14/810,979

(22) Filed: Jul. 28, 2015

(65) Prior Publication Data

US 2017/0027610 A1    Feb. 2, 2017

(51) Int. Cl.
| | | |
|---|---|---|
| *A61B 17/10* | (2006.01) | |
| *A61B 17/04* | (2006.01) | |
| *A61B 17/34* | (2006.01) | |
| *A61B 17/115* | (2006.01) | |
| *A61B 17/068* | (2006.01) | |
| *A61L 2/00* | (2006.01) | |
| *A61B 17/00* | (2006.01) | |
| *A61B 90/00* | (2016.01) | |

(52) U.S. Cl.
CPC ........ *A61B 17/3496* (2013.01); *A61B 17/068* (2013.01); *A61B 17/1155* (2013.01); *A61L 2/00* (2013.01); *A61B 2017/00477* (2013.01); *A61B 2090/0801* (2016.02); *A61B 2090/0813* (2016.02)

(58) Field of Classification Search
CPC .............. A61B 17/068; A61B 17/3496; A61B 2017/320044; A61B 17/3417; A61B 2017/00473; A61B 2017/00862; A61B 17/0493; A61B 1/00071; A61B 2017/00296; A61B 2017/00592; A61L 2/00

USPC ........... 227/175.1–182.1; 606/139, 142, 143
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |

(Continued)

FOREIGN PATENT DOCUMENTS

| | | |
|---|---|---|
| CA | 908529 A | 8/1972 |
| DE | 1057729 B | 5/1959 |

(Continued)

OTHER PUBLICATIONS

Extended European Search Report for Application No. 16181411 dated Dec. 1, 2016.

*Primary Examiner* — Robert Long

(57) ABSTRACT

A surgical system including a surgical instrument and a protection device is included. The surgical system includes a surgical instrument having an extension assembly releasably coupled thereto. The extension assembly includes a trocar member disposed within a distal end of the extension assembly and the trocar member includes an engagement feature defined in an outer surface thereof. The protection device is releasably coupled to the engagement feature of the trocar member, thereby providing a barrier adjacent a tip of the trocar member. A method of sterilizing a surgical instrument is also provided.

15 Claims, 8 Drawing Sheets

(56) References Cited

U.S. PATENT DOCUMENTS

| | | |
|---|---|---|
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,263,969 A * | 11/1993 | Phillips ............... A61F 2/0063 606/1 |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A * | 5/1994 | Grant ................ A61B 17/115 227/179.1 |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicola |
| 6,302,311 B1 | 10/2001 | Adams et al. |
| 6,338,737 B1 | 1/2002 | Toledano |

(56) References Cited

U.S. PATENT DOCUMENTS

| | | |
|---|---|---|
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicola |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicola |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,434,717 B2 * | 10/2008 | Shelton, IV .......... A61B 17/105 227/175.1 |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,651,017 B2 * | 1/2010 | Ortiz .................... A61B 17/064 227/176.1 |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |

(56) References Cited

U.S. PATENT DOCUMENTS

| | | |
|---|---|---|
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2004/0093024 A1* | 5/2004 | Lousararian ....... A61B 17/0057 606/213 |
| 2005/0051597 A1 | 3/2005 | Toledano |
| 2005/0059865 A1* | 3/2005 | Kahle ................ A61B 17/3423 600/206 |
| 2005/0107813 A1 | 5/2005 | Gilete Garcia |
| 2005/0119669 A1* | 6/2005 | Demmy ............... A61B 17/068 606/139 |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0016799 A1* | 1/2010 | Schweitzer ........ A61B 17/3462 604/167.01 |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0234687 A1* | 9/2010 | Azarbarzin ............ A61B 17/29 600/201 |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |

(56) References Cited

U.S. PATENT DOCUMENTS

| | | |
|---|---|---|
| 2013/0060258 A1 | 3/2013 | Giacomantonio |
| 2013/0066156 A1* | 3/2013 | Seo .................... A61B 17/3423 600/204 |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2017/0340348 A1* | 11/2017 | Cabrera ................ A61B 17/34 |

FOREIGN PATENT DOCUMENTS

| | | |
|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2524656 A2 | 11/2012 |
| EP | 2676617 A1 | 12/2013 |
| EP | 3023077 A1 | 5/2016 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 2001/054594 A1 | 8/2001 |
| WO | 2008/107918 A1 | 9/2008 |

* cited by examiner

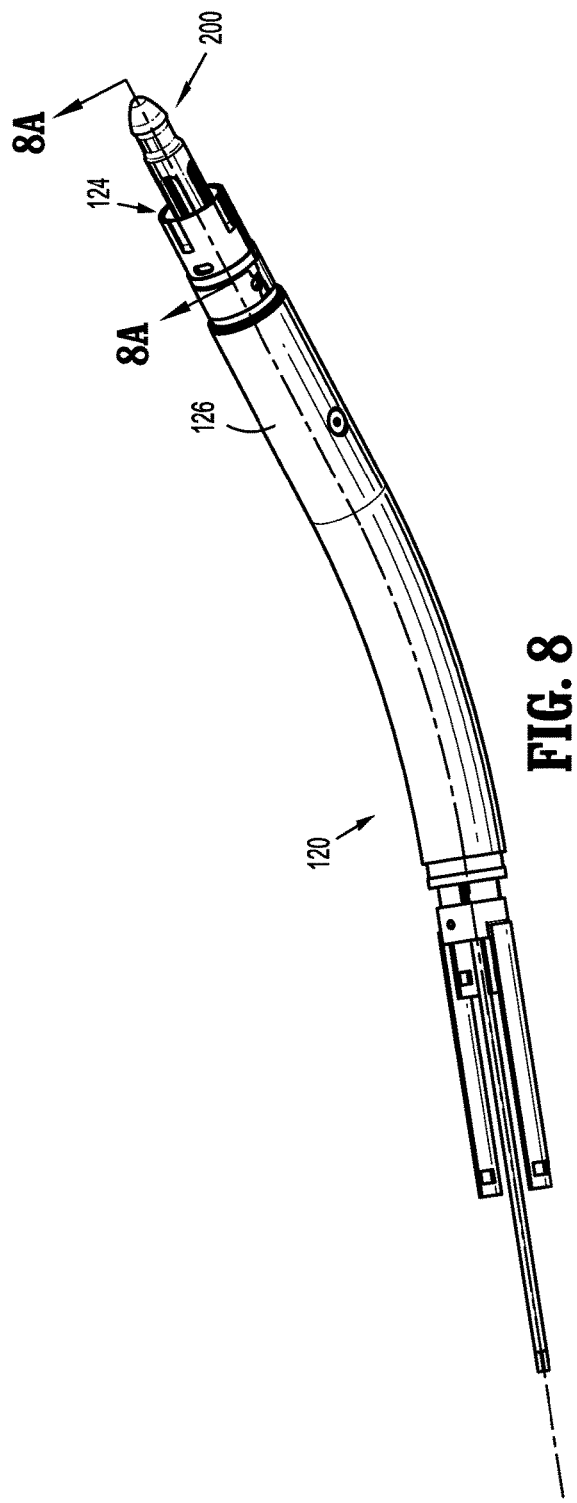
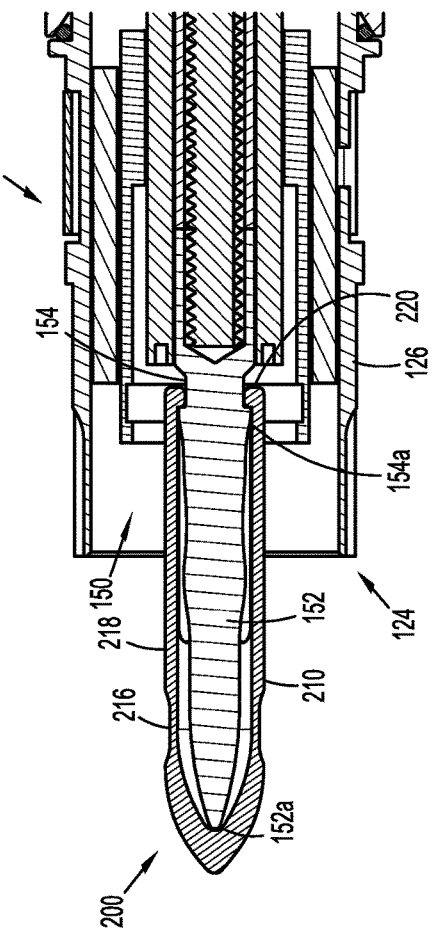
FIG. 8
FIG. 8A

TROCAR TIP PROTECTOR

BACKGROUND

1. Technical Field

The present disclosure relates generally to surgical stapling devices. More specifically, the present disclosure relates to selectively removable protection devices for reusable adapter and extension assemblies for actuation units of surgical stapling devices.

2. Background of Related Art

Powered and manual surgical stapling devices for used in surgical procedures typically include a handle assembly and an end effector. To permit reuse of the handle assemblies of these surgical stapling devices and so that the handle assembly may be used with a variety of end effectors, adapter assemblies and extension assemblies have been developed for selective attachment to the handle assemblies and to a variety of end effectors. Following use, the adapter and/or extension assemblies may be sterilized for reuse.

Many adapter assemblies and extension assemblies include a trocar protruding from a distal end. The trocar may be used to puncture tissue and act as a guide to more easily align the adapter or extension assembly with the end effector. In order to facilitate the puncturing of tissue, the trocar typically includes a sharp distal tip.

In instances where an adapter or extension assembly having a trocar is used during the surgical procedure, in preparation for sterilization procedures, the trocar of the adapter and/or extension assembly may be exposed, presenting a puncture or laceration risk to operating room personnel or others handling the assembly. Therefore, a need exists for removable protection devices for reusable adapter and extension assemblies for actuation units of powered and/or manual surgical stapling devices.

SUMMARY

The present disclosure is directed to a surgical system including a surgical instrument and a protection device. The surgical instrument includes an extension assembly releasably coupled thereto and includes a trocar member disposed within a distal end thereof. The trocar member includes an engagement feature defined in an outer surface thereof. The protection device is releasably coupled to the engagement feature of the trocar member, thereby providing a barrier adjacent to a tip of the trocar member.

The protection device may also include a plurality of legs disposed on a first end thereof and extending axially therefrom.

The plurality of legs may terminate in a bard defined on an inner surface thereof. The barb may be configured to releasably engage the engagement feature of the trocar member of the surgical instrument.

The engagement feature of the trocar member may be a lip defined in the outer surface thereof. The lip may be configured to engage a complimentary engagement feature disposed on the protection device.

A second end of the protection device may include a conical configuration defining a blunt tip, thereby inhibiting a clinician from contacting the tip of the trocar member.

The protection device may include an annular groove defined in an outer surface thereof configured to allow grasping of the protection device.

The protection device may be formed from a material that is suitable for use in a sterilization process.

The second end of the protection device may define a planar configuration.

The second end of the protection device may include a flange disposed thereon. The flange may be configured for grasping.

The second end of the protection device may include a rectangular base having an outer perimeter greater than an outer diameter of a housing of the surgical instrument. The second end of the protection device may include a flange having an outer diameter greater than an outer diameter of a housing surrounding the trocar member.

According to another aspect, the present disclosure is directed to a method for sterilizing a surgical device. The method includes providing a surgical instrument having an extension assembly releasably coupled thereto. The extension assembly includes a trocar member disposed within a distal end thereof, wherein at least a portion of the trocar member protrudes from the distal end of the extension assembly. The trocar member includes an engagement feature defined within an outer surface thereof.

The method further includes providing a protection device configured to be releasably coupled to the engagement feature of the trocar member, advancing the protection device over the trocar member and partially within a cavity defined within the distal end of the extension assembly until the protection device releasably engages the engagement feature of the trocar member, thereby providing a barrier adjacent to the pointed distal tip of the trocar member, removing the extension assembly, with the protection device releasably attached thereto, from the surgical instrument, and placing the extension assembly, with the protection device releasably attached thereto, into a sterilization chamber.

The method may also include the protection device having a plurality of legs disposed on a distal end thereof. The plurality of legs may extend axially from the distal end of the protection device and terminate in a barb defined on an inner surface thereof. Each barb of the plurality of legs may engage the engagement feature of the trocar member, thereby releasably coupling the protection device to the trocar member.

The method may include the proximal end of the protection device having a conical configuration defining a blunt tip, thereby inhibiting a clinician from contacting the pointed distal tip of the trocar member.

The protection device may have an annular groove defined in an outer surface thereof configured to allow grasping of the elongate body.

The method may include the protection device being constructed of a material suitable for use in a sterilization process.

The method may include the proximal end of the protection device defining a planar configuration, thereby inhibiting a clinician from contacting the pointed distal tip of the trocar member.

The method may include the proximal end of the protection device including a flange disposed thereon configured for grasping.

The method may include the surgical instrument having an adapter assembly configured to be selectively secured to the surgical instrument on a first end and selectively secured to the extension assembly on a second end.

The method may include placing the adapter assembly and the extension assembly, including the protection device releasably attached thereto, into a sterilization chamber.

BRIEF DESCRIPTION OF THE DRAWINGS

The above and other aspects, features, and advantages of the present disclosure will become more apparent in light of the following detailed description when taken in conjunction with the accompanying drawings in which:

FIG. 4A is a side, cross-sectional view, of the trocar assembly of FIG. 1, taken along line 4A-4A;

FIG. 8 is a perspective view of the trocar tip protector of FIG. 6 advanced over a trocar of the extension assembly of FIG. 2;

FIG. 8A is side, cross-sectional view, of the distal end of the extension assembly of FIG. 8, taken along line 8A-8A;

DETAILED DESCRIPTION OF EMBODIMENTS

Figure 1:
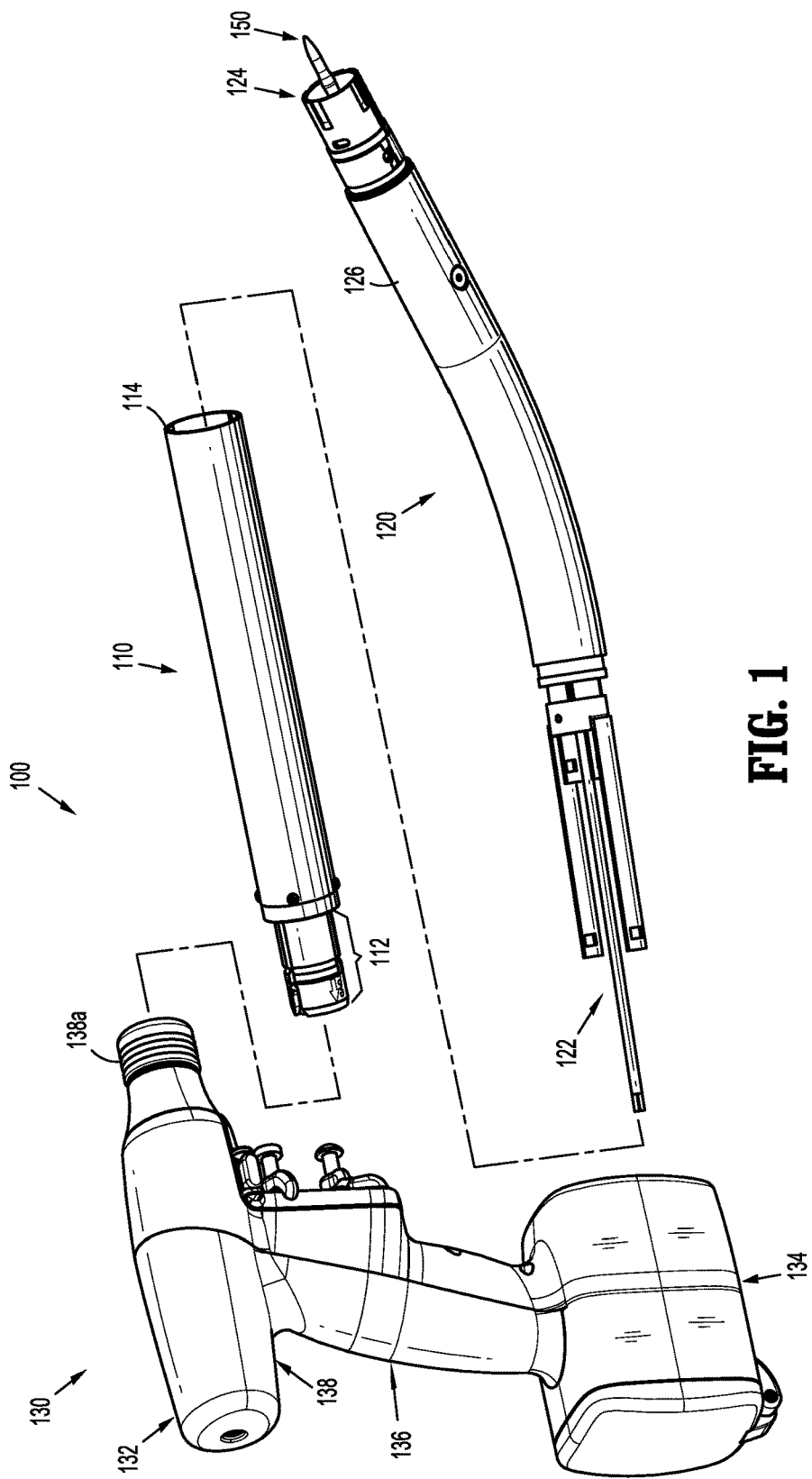
FIG. 1 is a perspective view of a powered surgical stapling device suitable for use with a trocar tip protector in accordance with embodiments of the present disclosure, with parts separated.

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Figure 2:
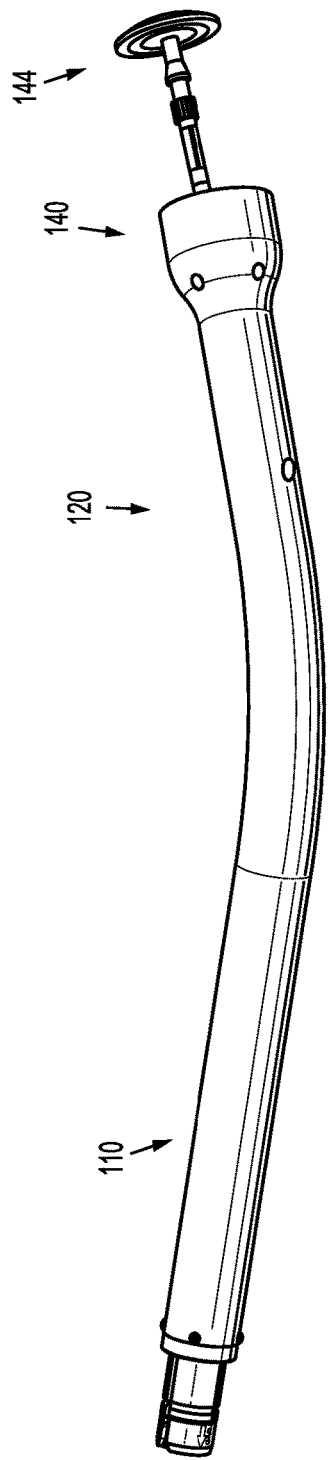
FIG. 2 is a side view of an adapter assembly and an extension assembly of the powered surgical stapling device of FIG. 1, shown with a loading unit and anvil assembly attached thereto.

With reference to FIG. 1, a powered surgical stapling device (surgical instrument) suitable for use with a trocar tip protector (protection device) 200 (FIG. 5) is illustrated and generally identified by reference numeral 100. Powered surgical stapling device 100 includes an adapter assembly 110, an extension assembly 120, and a handle assembly 130. As illustrated in FIG. 1, handle assembly 130 is configured for selective connection with adapter assembly 110, and, in turn, adapter assembly 110 is configured for selective connection with extension assembly 120. Extension assembly 120 is configured for selective connection with a circular loading unit 140 (FIG. 2) and an anvil assembly 144 (FIG. 2), for applying a circular array of staples (not shown) to tissue (not shown).

Handle assembly 130 includes a handle housing 132 and a lower housing portion 134, an intermediate housing portion 136 extending from and/or supported on a lower housing portion 134, and an upper housing portion 138 extending form and/or supported on intermediate housing portion 136. A distal half-section of upper housing portion 138 defines a nose or connecting portion 138a configured to accept a corresponding drive coupling assembly (not shown) of adapter assembly 110. For a detailed description of the structure and function of an exemplary surgical device, please refer to commonly owned U.S. Patent Application Publication No. 2012/0253329, the content of which is incorporated by reference herein in its entirety.

Adapter assembly 110 includes a proximal end 112 configured for operable connection to connecting portion 138a of handle assembly 130 and a distal end 114 configured for operable connection to extension assembly 120. For a detailed description of the structure and function of an exemplary adapter assembly, please refer to commonly owned U.S. Pat. Appl. Publ. No. 2012/0253329, the contents of which is incorporated by reference herein in its entirety.

Extension assembly 120 is configured to operably connect adapter assembly 110 with a circular loading unit 140 (FIG. 2) and an anvil assembly 144 (FIG. 2) for applying a circular array of staples (not shown) to tissue (not shown). Extension assembly 120 includes a proximal end 122 configured to operably connect with distal end 114 of adapter assembly 110. Distal end 124 of extension assembly 120 is configured to operably connect with loading unit 140 and anvil assembly 144. It is contemplated that any suitable loading unit, anvil assembly, and adapter assembly may be utilized with extension assembly 120. Exemplary loading units and anvil assemblies are described in commonly owned U.S. Pat. No. 8,590,763 and U.S. patent application Ser. Nos. 14/056,301 and 14/149,355, the contents of each being incorporated herein by reference in their entirety.

Figure 3:
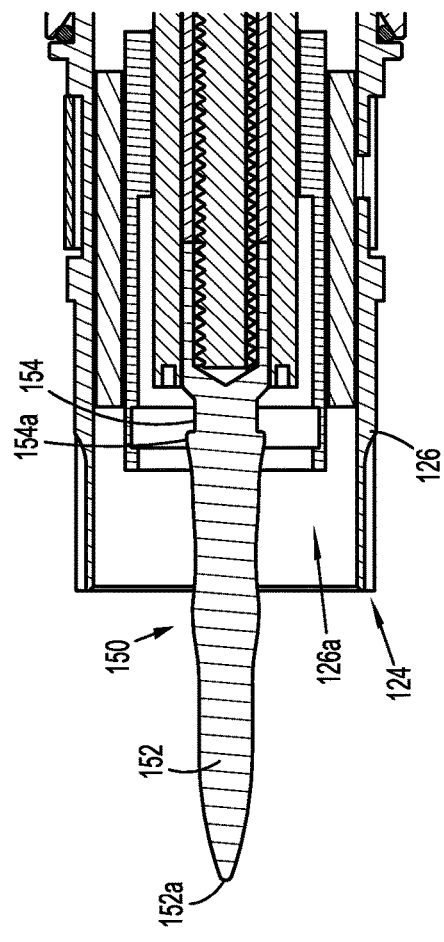
FIG. 3 is a side, cross-sectional view, of a distal end of the extension assembly of the powered surgical stapling device of FIG. 1 with an anvil assembly of FIG. 2 removed.
Figure 4:
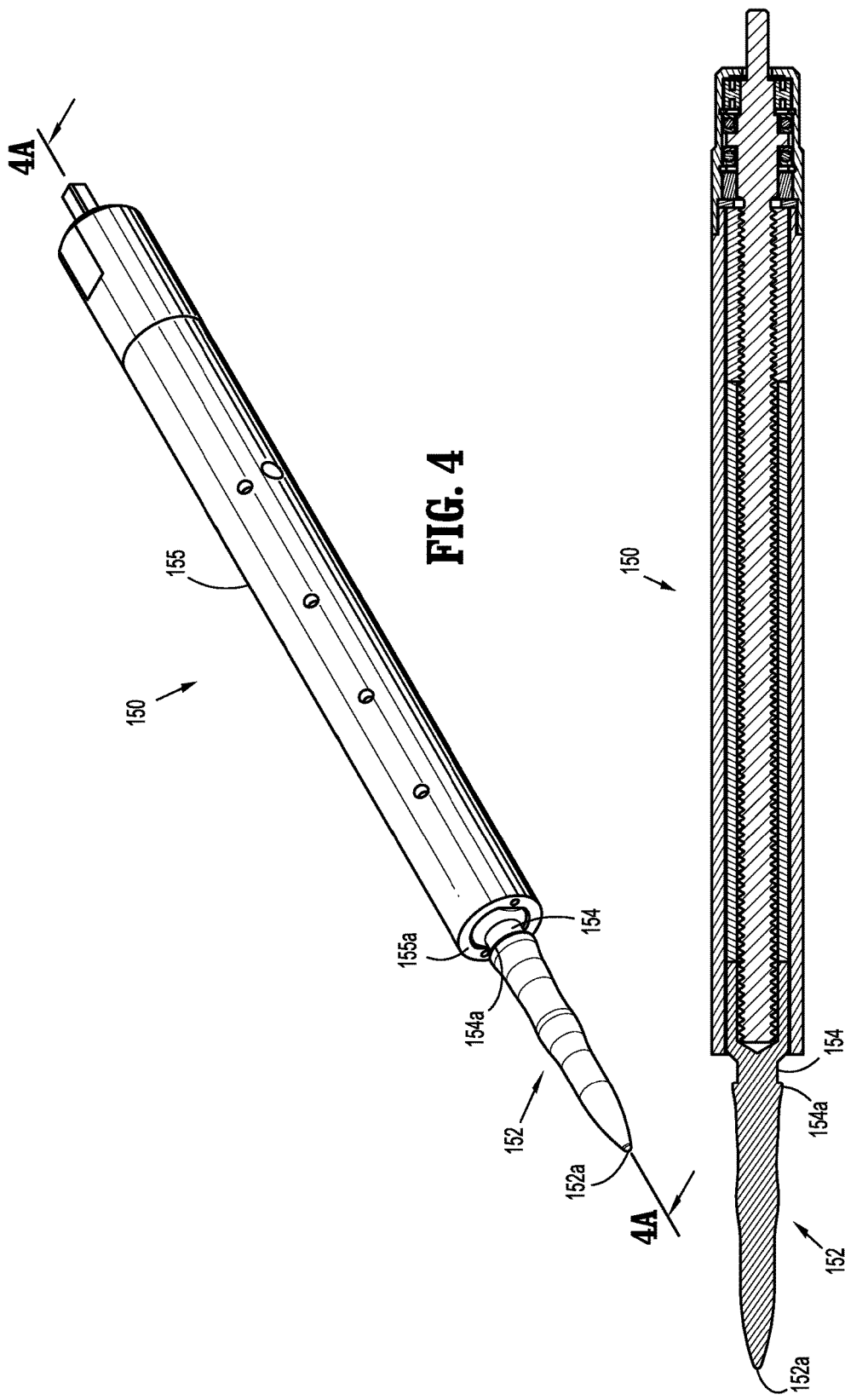
FIG. 4 is a front, perspective view, of a trocar assembly of the extension of FIG. 1.
Figure 5:
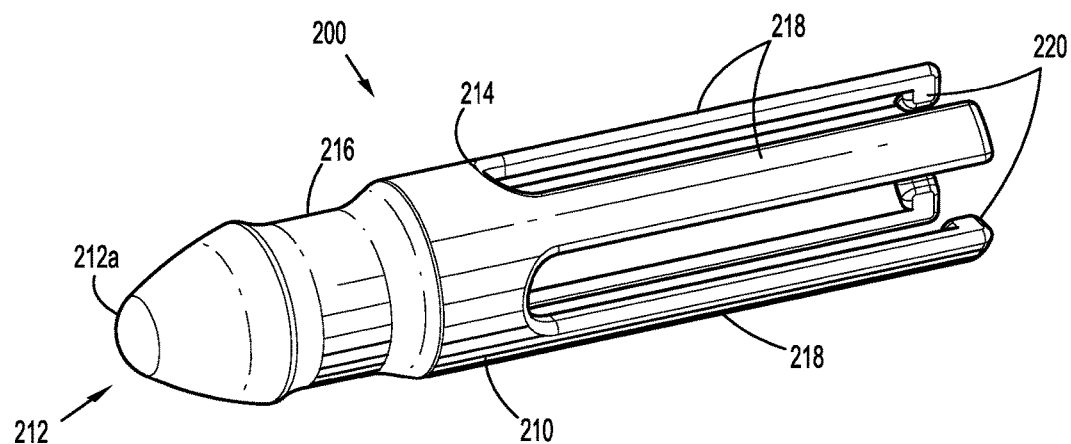
FIG. 5 is a front, perspective view, of a trocar tip protector provided in accordance with an exemplary embodiment of the present disclosure.

Extension assembly 120 includes a trocar assembly 150 (FIGS. 3, 4, and 4A) disposed within an outer sleeve 126 of extension assembly 120 and protruding from distal end 124, as best illustrated in FIG. 3. Trocar assembly includes a housing 155 with a distal end 155a. A distal end of trocar assembly 150 includes a trocar member 152 defining a generally cylindrical configuration having a pointed tip 152a. A proximal end of trocar member 152 includes an annular groove 154 defined within an outer surface thereof and forming a proximal facing lip 154a adapted to selectively engage anvil assembly 144. With reference to FIG. 5, an exemplary embodiment of a trocar tip protector (protection device) provided in accordance with the present disclosure is illustrated and generally identified by reference numeral 200. Trocar tip protector 200 includes an elongate body 210 including a proximal end 212 and a distal end 214. Although elongate body 210 is shown as generally including a circular cross section, it is contemplated that elongate body 210 may include any suitable shape, such as square, rectangular, octagonal, or the like. Proximal end 212 is generally shown as defining a generally conical shape, defining a blunt tip 212a. A recess 216 is defined in an outer surface of elongate body 210 and is adapted to enable a clinician to easily grasp elongate body 210. Although shown as generally having a circular shape, it is contemplated that recess 216 may include any suitable shape enabling ease of grasping. A plurality of legs 218 extend distally from distal end 214 and terminate in a barb 220. Barb 220 of each leg 218 extends radially inward such that barb 220 may releasably engage annular groove 154 of trocar member 152. In this manner, barb 220 is prohibited from passing distally over proximal facing lip 154a of annular groove 154 without external force (e.g., legs 218 deflecting up and over lip 154a). As best illustrated in FIGS. 8 and 8A, trocar tip protector 200 advances over trocar member 154 until pointed distal tip 152a is positioned within body 210 of trocar tip protector 200, thereby inhibiting a clinician from contacting the sharp distal tip 152a. Although trocar tip protector 200 is generally shown having four legs, it is contemplated that any suitable number of legs may be employed to enable trocar tip protector 200 to releasably engage annular groove 154 of trocar member 152, such as two, three, five, six, etc. As can be appreciated, trocar tip protector 200 may be constructed of any suitable material for use during a sterilization process, such as a metallic, polymeric, or composite material.

In operation, with reference to FIGS. 1-7, after a procedure is performed on a patient and the loading unit 140 has been fired, extension assembly 120 may be removed from adapter assembly 110. It is also contemplated that both adapter assembly 110 and extension assembly 120 may be removed together from the handle assembly 130. After removing the extension assembly 120 from the adapter assembly 110, the anvil assembly 144 may be removed from trocar member 152 and thereafter, loading unit 140 may be removed from the distal end of extension assembly 120, thereby exposing the sharp distal tip 152a of trocar member 152. At this point, trocar tip protector 200 may be advanced over the pointed distal tip 152a of trocar member 152 and into a cavity 126a defined in the distal end 124 of outer sleeve 126 of extension assembly 120. Trocar tip protector 200 may continue to be advanced over the trocar member 152 until barbs 220 of trocar tip protector 200 fully engage annular groove 154 of trocar member 152 such that a portion of the trocar tip protector 200 is disposed within cavity 126a and trocar tip 152a is positioned within body 210. Trocar tip protector 200 thus provides a barrier adjacent the pointed distal tip 152a and inhibiting contact therewith by a clinician or other person. In this manner, the clinician or other person is protected from puncture wounds or abrasions that may result from contact with the pointed distal tip 152a. Extension assembly 120, with trocar tip protector 200 secured thereto, may then be placed into a suitable sterilization chamber and the sterilization process may begin. It is contemplated that the adapter assembly 110, extension assembly 120, and the trocar tip protector 200 may be placed within a suitable sterilization chamber as an assembled unit. After the sterilization process is complete, extension assembly 120, with trocar tip protector 200 remaining attached thereto, may be removed from a suitable sterilization chamber and set aside until a new loading unit 140 is ready to be installed thereon. Only at this point is trocar tip protector 200 removed from trocar member 152, thereby protecting a clinician from any abrasion or puncture wounds during the above described process.

Figure 6:
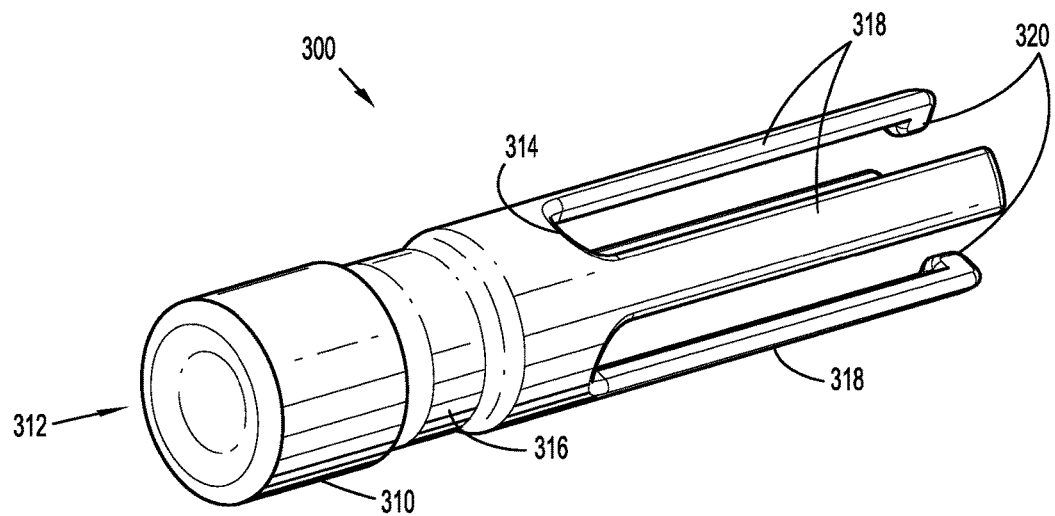
FIG. 6 is a front, perspective view, of another trocar tip protector provided in accordance with an exemplary embodiment of the present disclosure.

Referring now to FIG. 6, another embodiment of a trocar tip protector (protection device) provided in accordance with another exemplary embodiment of the present disclosure is illustrated and generally identified by reference numeral 300. Trocar tip protector 300 includes body 310, recess 316, and barbs 320 on legs 318 which extend from distal end 314 of body 310. Thus, trocar tip protector 300 is substantially similar to trocar tip protector 200 except that the proximal end 312 defines a generally planar configuration. In operation, trocar tip protector 300 is utilized in a similar fashion to that of trocar tip protector 200, and therefore, in the interest of brevity, a detailed description of the operation of trocar tip protector 300 will not be given herein.

Figure 7:
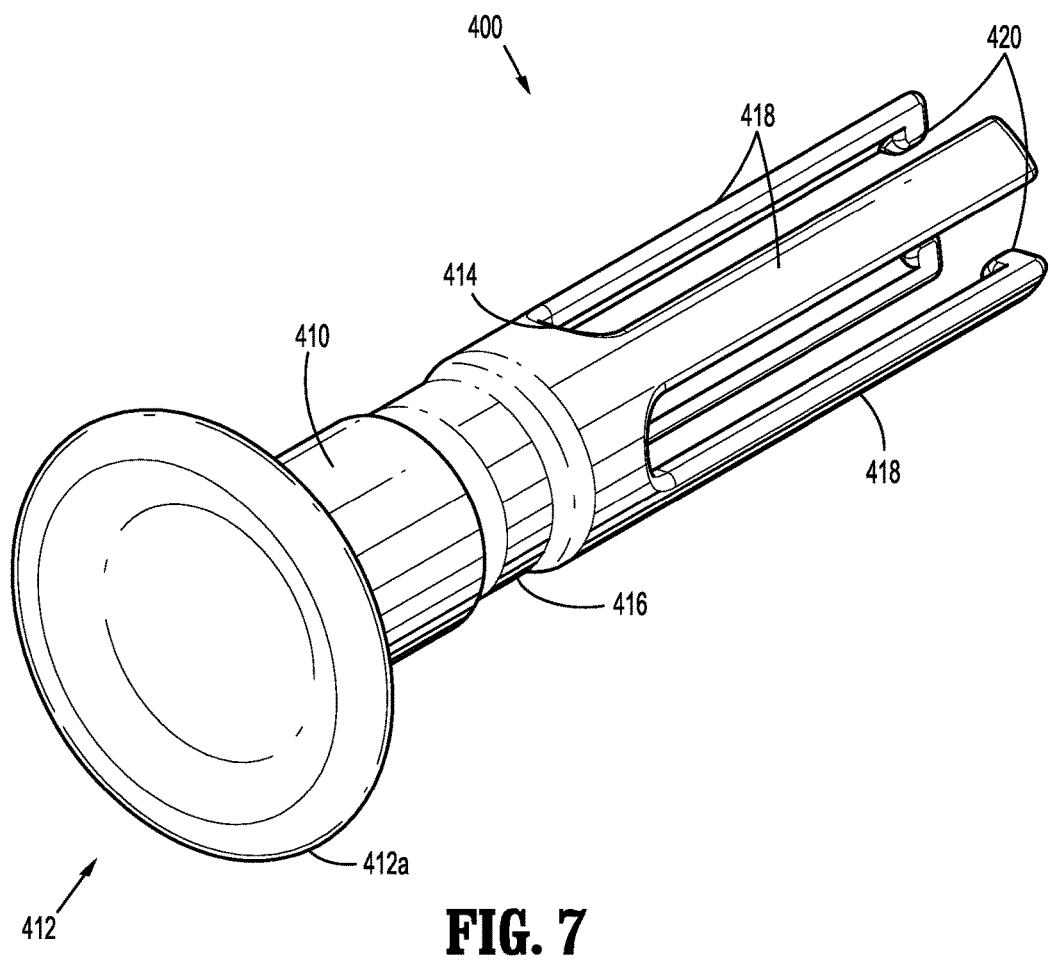
FIG. 7 is a front, perspective view, of another trocar tip protector provided in accordance with an exemplary embodiment of the present disclosure.

Turning now to FIG. 7, yet another exemplary embodiment of a trocar tip protector (protection device) in accordance with the present disclosure is illustrated and generally identified by reference numeral 400. Trocar tip protector 400 includes body 410, recess 416, and barbs 420 on legs 418 which extend from distal end 414 of body 410. Thus, trocar tip protector 400 is substantially similar to trocar tip protector 200 except that the proximal end 412 includes a flared distal end defining a flange 412a having circular shape with an outer diameter greater than that of elongate body 410. The larger outer diameter of the flange 412a provides a large surface area for the clinician to grasp. Although the proximal surface 412b of proximal end 412 is generally shown as having a depression formed therein, it is contemplated that the proximal surface 412b may include any suitable shape, such as convex, planar, or the like. In operation, trocar tip protector 400 is utilized in a similar fashion to that of trocar tip protector 200, and therefore, in the interest of brevity, a detailed description of the operation of trocar tip protector 400 will not be given herein.

Figure 9:
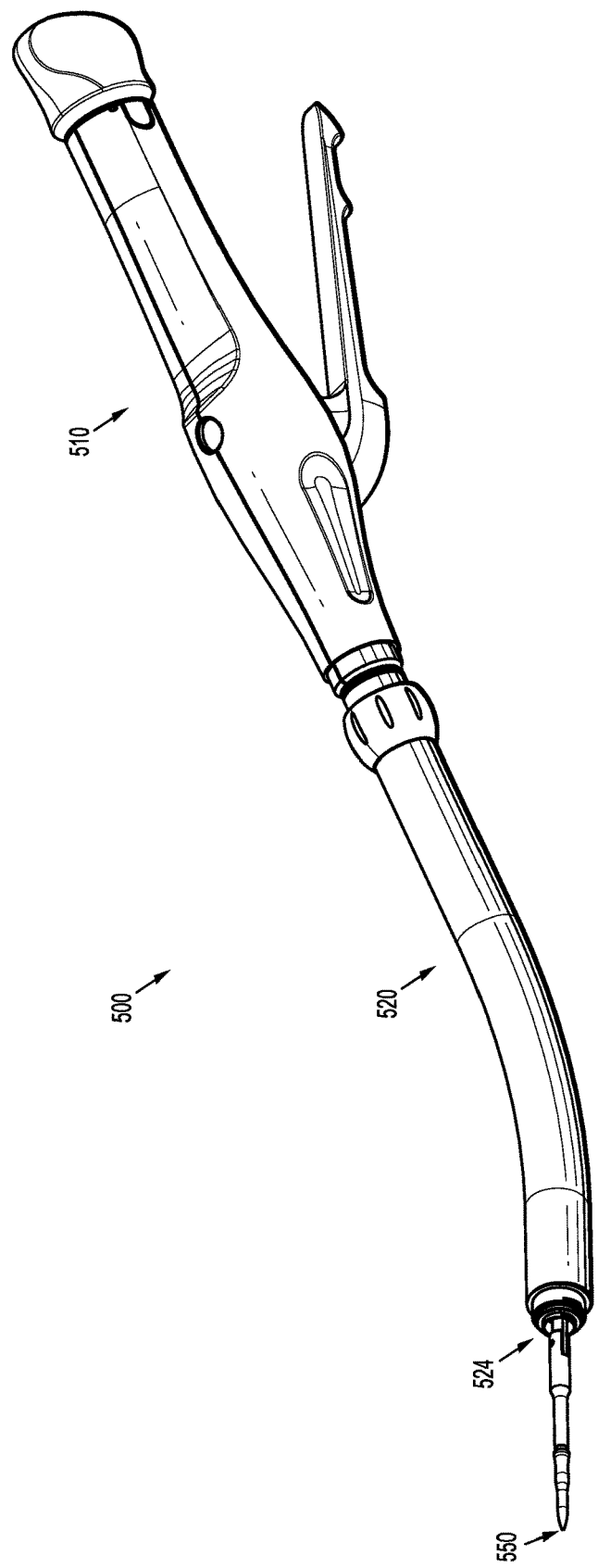
FIG. 9 is a perspective view of a manual surgical stapling device suitable for use with the trocar tip protector in accordance with the present disclosure.

While the trocar tip protectors have been described herein with respect to powered stapling devices, it should of course be understood that the present trocar tip protectors are also suitable for use with manual stapling devices. For example, referring to FIG. 9, a manual surgical stapling device suitable for use with a trocar tip protector in accordance with the present disclosure is illustrated and generally identified by reference numeral 500. Manual surgical stapling device 500 generally includes a handle assembly 510, extension assembly 520, extending distally therefrom and terminating in a distal end 524. A trocar assembly 550 is disposed within extension assembly 520 and extends distally therefrom. Trocar assembly 550 is similar to that of trocar assembly 150 of extension assembly 120, described above, and therefore, in the interest of brevity, details of trocar assembly 150 will not be discussed in detail herein. For a detailed description of the structure and function of an exemplary manual surgical stapling device, reference may be made to U.S. Patent Application Publication No. 2014/0263548, the content of which is incorporated by reference herein in its entirety. In operation, a trocar tip protector may be selectively secured to trocar assembly 150 in a similar fashion to the method described above with respect to a powered surgical device 100.

Figure 10:
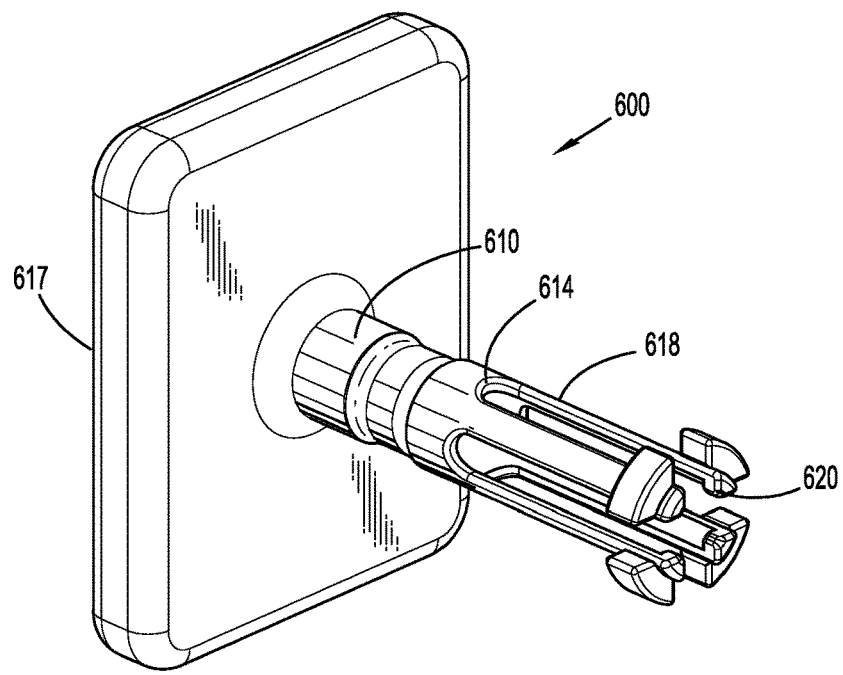
FIG. 10 is a perspective view of another trocar tip protector provided in accordance with an exemplary embodiment of the present disclosure.
Figure 11:
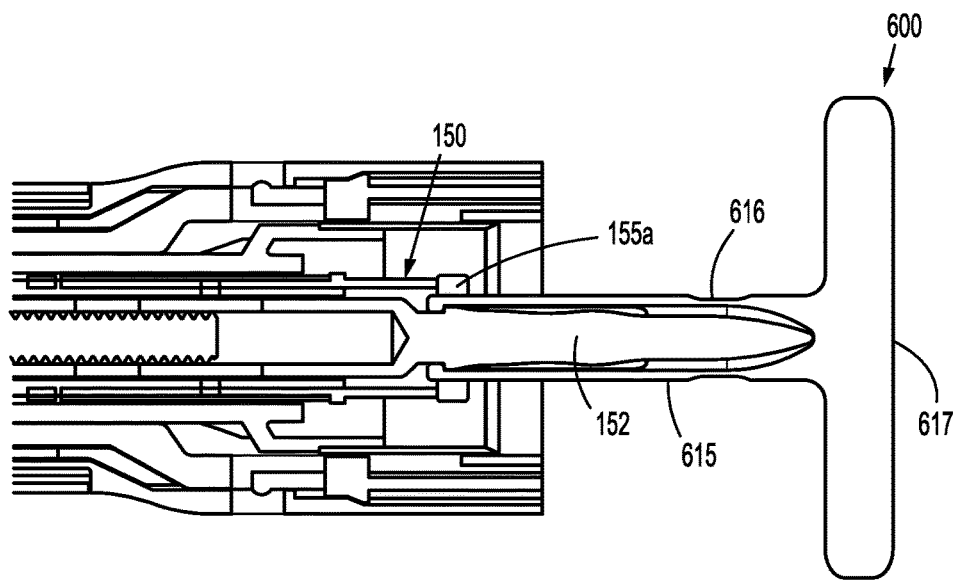
FIG. 11 is a side cross-sectional view of the trocar tip protector of FIG. 10 advanced over a trocar of the extension assembly of FIG. 2.

Referring now to FIGS. 10 and 11, another exemplary embodiment of a trocar tip protector (protection device) in accordance with the present disclosure is illustrated and generally identified by reference numeral 600. Trocar tip protector 600 includes body 610, recess 616, and barbs 620 on legs 618 which extend from distal end 614 of body 610. Thus, trocar tip protector 600 is substantially similar to previously disclosed trocar tip protectors 200, 300, 400 except that proximal end 612 includes a rectangular base 617. Rectangular base 617 has an outer perimeter that is greater than an outer diameter of body 610 and an outer diameter of loading unit 140. The rectangular configuration of base 617 provides a larger surface area than that of proximal end 312 (FIG. 6) of trocar tip protector 300 and flange 412a (FIG. 7) of trocar tip protector 400. This increased surface area of base 617 allows the base 617 to be placed on a horizontal surface (e.g., table, countertop, etc.) so that the clinician may push the adapter assembly 110 towards the trocar tip protector 600 such that the protruding pointed tip 152*a* of trocar assembly 150 is received in body 610, thereby inhibiting a clinician from contacting the sharp distal tip 152*a*. The increased surface area of the base 617 provides a high degree of stability and reduces the likelihood that base 617 will move or wobble while the clinician is inserting the pointed tip 152*a* into body 610. Additionally, trocar tip protector 600 has a flange 615 located proximally of recess 616. Flange 615 has an outer diameter that is greater than distal end 614 and legs 618. The outer diameter of flange 615 is also greater than an outer diameter of the housing 155 of trocar assembly 150. As the outer diameter of the flange 615 is greater than the outer diameter of the housing 155, the trocar tip protector 600 inhibits the clinician from fully retracting the trocar assembly 150 while the trocar tip protector 600 is coupled to the trocar assembly 150. The amount of proximal movement of the trocar member 152 is limited as proximal movement of the trocar member 152 will cause corresponding proximal movement of the trocar tip protector 600 until the flange 615 abuts the distal end 155*a* of the housing 155, thereby inhibiting further proximal movement of the trocar member 152.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical system, comprising:
   a surgical instrument including an extension assembly releasably coupled thereto, the extension assembly including a trocar member disposed within a distal end of the extension assembly and extending therefrom, the trocar member terminating at a tissue piercing tip, the trocar member including an annular groove defined in an outer surface thereof; and
   a protection device defining a cavity therein configured to receive a portion of the trocar member therein such that the tissue piercing tip of the trocar member is enveloped by the protection device, wherein the protection device is releasably coupled to the annular groove of the trocar member thereby providing a barrier adjacent the tissue piercing tip of the trocar member,
   wherein the protection device further includes a plurality of legs disposed on a first end portion thereof, the plurality of legs extending axially therefrom,
   wherein a second end portion of the protection device defines a planar configuration, the second end portion of the protection device including a rectangular base having an outer perimeter greater than an outer diameter of a housing of the surgical instrument.

2. The surgical system according to claim 1, wherein the plurality of legs terminate in a barb defined on an inner surface thereof, the barb configured to releasably engage the annular groove of the trocar member of the surgical instrument.

3. The surgical system according to claim 1, wherein the annular groove of the trocar member is a lip defined in the outer surface thereof, the lip configured to engage a complimentary engagement feature disposed on the protection device.

4. The surgical system according to claim 1, wherein a second end portion of the protection device includes a conical configuration defining a blunt tip, thereby inhibiting a clinician from contacting the tip of the trocar member.

5. The surgical system according to claim 1, wherein an annular groove is defined in an outer surface of the protection device, the annular groove configured to allow grasping of the protection device.

6. The surgical system according to claim 1, wherein the protection device is formed from a material suitable for use in a sterilization process.

7. The surgical system according to claim 1, wherein a second end portion of the protection device includes a flange disposed thereon configured for grasping.

8. The surgical system according to claim 1, wherein the second end portion of the protection device includes a flange having an outer diameter greater than an outer diameter of a housing surrounding the trocar member.

9. A method of sterilizing a surgical device, comprising:
   providing a surgical instrument, including an extension assembly releasably coupled to the surgical instrument including a trocar member disposed within a distal end portion thereof and extending therefrom, the trocar member terminating at a tissue piercing tip, wherein at least a portion of the trocar member protrudes from the distal end portion of the extension assembly, the trocar member including an annular groove defined within an outer surface thereof;
   providing a protection device defining a cavity therein configured to receive a portion of the trocar member therein such that the tissue piercing tip of the trocar member is enveloped by the protection device, wherein the protection device is configured to be releasably coupled to the annular groove of the trocar member,
   wherein the protection device further includes a plurality of legs disposed on a first end portion thereof, the plurality of legs extending axially therefrom,
   wherein a second end portion of the protection device defines a planar configuration, the second end portion of the protection device including a rectangular base having an outer perimeter greater than an outer diameter of a housing of the surgical instrument;
   advancing the protection device over the trocar member and partially within a cavity defined within the distal end portion of the extension assembly until the protection device releasably engages the annular groove of the trocar member, thereby providing a barrier adjacent the tissue piercing tip of the trocar member;
   removing the extension assembly, with the protection device releasably attached thereto, from the surgical instrument; and
   placing the extension assembly, with the protection device releasably attached thereto, into a sterilization chamber.

10. The method according to claim 9, wherein providing a protection device includes the plurality of legs terminating in a barb defined on an inner surface thereof, wherein each barb of the plurality of legs engages the annular groove of the trocar member, thereby releasably coupling the protection device to the trocar member.

11. The method according to claim 9, wherein providing a protection device includes the protection device having an annular groove defined in an outer surface of thereof, the annular groove configured to allow grasping of the elongate body.

12. The method according to claim 9 wherein providing a protection device includes the protection device is constructed of a material suitable for use in a sterilization process.

13. The method according to claim 9, wherein providing a protection device includes a second end portion of the protection device including a flange disposed thereon configured for grasping.

14. The method according to claim 9, wherein providing a surgical instrument further includes an adapter assembly configured to be selectively secured to the surgical instrument on a first end and selectively secured to the extension assembly on a second end.

15. The method according to claim 14, wherein placing the extension assembly, with the protection device releasably attached thereto, into a sterilization chamber includes placing the adapter assembly and the extension assembly, including the protection device releasably attached thereto, into a sterilization chamber.

\* \* \* \* \*